United States Patent [19]
Curtis

[11] Patent Number: 4,753,647
[45] Date of Patent: Jun. 28, 1988

[54] INFANT GARMENT

[76] Inventor: Jamie L. Curtis, 1416 N. Havenhurst Dr., #6C, Los Angeles, Calif. 90046

[21] Appl. No.: 16,832

[22] Filed: Feb. 20, 1987

[51] Int. Cl.<sup>4</sup> ............................................. A61M 13/16
[52] U.S. Cl. ................................................. 604/385 R
[58] Field of Search .............................. 604/385.1, 358

[56] References Cited

U.S. PATENT DOCUMENTS 4,221,221  9/1980  Ehrlich .................... 604/385.1 X
4,417,894  11/1983  Norris ........................ 604/385.1

Primary Examiner—John D. Yasko
Attorney, Agent, or Firm—Kolisch, Hartwell & Dickinson

[57] ABSTRACT

A disposable infant garment which takes the form of a diaper including, on its outer side, a sealed, but openable, moisture-proof pocket which contains one or more clean-up wipers.

1 Claim, 1 Drawing Sheet

INFANT GARMENT

BACKGROUND AND SUMMARY OF THE INVENTION

The present invention relates to a disposable infant garment, and more particularly, to a diaper combined with an outer, moisture-proof pocket that contains one or more clean-up wipers.

A routine which is repetitively familiar to parents of infants everywhere, involves the handling of soiled diapers, and the infant cleanup which follows.

The introduction, in the not too distant past, of so-called disposable diapers has, by addressing the diaper-washing and re-use consideration, offered a significant advance in this field. Likewise, recent introduction of prepackaged clean-up wipers has provided a simplifying advance in dealing with clean-up activity.

Nevertheless, and despite these worthy contributors toward simplifying infant care, there is still room for important improvement. For example, until now, diapers and wipers have been sold, stored and handled as two different, separate, independent entities. So, one making use of these products, both at home and while traveling, must necessarily store, dispense, and travel with, etc., two separately packaged items. Quite apart from these issues, there is the further consideration about the convenience of bringing the two (separate diaper and separate wiper) into necessary proximity when an infant's diaper is to be removed for changing, and a clean-up conducted.

A general and important object of the present invention, therefore, is to provide a unique infant garment which addresses these issues in a practical and extremely satisfactory manner, and which offers another significant advance in the simplification of infant care.

More specifically, an object of this invention is to provide such a garment which takes the form of a disposable diaper that self-contains one or more sealed-in clean-up wipers which are instantly removable and usable, on-the-scene, so-to-speak, all of the time.

According to a preferred embodiment of the invention, a garment is proposed which includes a diaper, on the outer side of which is formed a moisture-impervious pocket adapted to contain (and which preferably, as manufactured, does contain) a sealed-in clean-up wiper (or more than one, if so desired).

The advantages of such a garment are immediately apparent: diapers and wipers are not separately handled, separately packaged, products. Wipers are always immediately on-the-scene available for use.

These and other important features and advantages that are offered by the invention will become more fully apparent as the description which now follows is read in conjunction with the accompanying drawings.

DETAILED DESCRIPTION OF THE INVENTION

Figure 1:
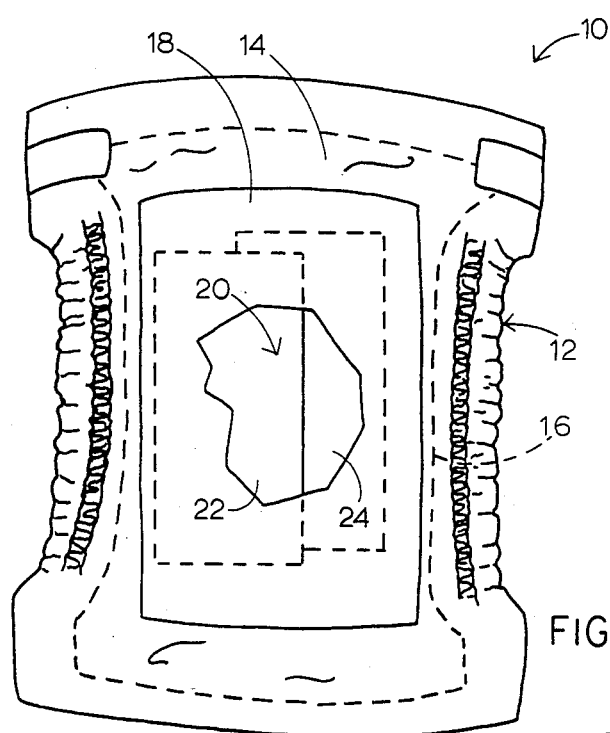
FIG. 1 is a plan view of a flattened-out infant garment constructed in accordance with the invention. A central, frontal pocket fragment has been removed to expose a pair of stored clean-up wipers.

Turning now to the drawings, and referring first of all to FIG. 1, indicated generally at 10 is an infant garment which is constructed in accordance with a preferred embodiment of the present invention. Forming a part of garment 10 is a diaper 12 which is, generally speaking, conventional in construction. Thus, the diaper, on its outer side (which faces the viewer in FIG. 1), is formed with a suitable thin, moisture-impervious material 14. The central portion of side 14 is referred to herein as a moisture-impervious expanse.

Suitably and conventionally joined to material 14, on the side thereof which faces away from the viewer in FIG. 1, is the usual moisture-absorbant structure 16 which, of course, lies against an infant's body with the diaper in use. Structure 16 defines what is referred to herein as the inner side of the diaper.

The left and right sides of diaper 12, as the same is seen in FIG. 1, are puckered, or gathered, by the usual bands of elastomers which enable these edges to cling to, and ride fairly closely around, an infant's legs.

Also included in garment 10, on the central expanse of diaper side 14, is a sheet 18 of a moisture-impervious material, which may be the same material that is used to form side 14. In what might be thought of as a pre-use condition for garment 10, sheet 18 is perimetrally attached to and sealed with the outer side of side 14. Thus, along with material 14, it forms an elongate, moisture-impervious pocket 20 which, herein, and still considering the so-called "pre-use condition", contains two clean-up wipers shown at 22, 24. This organization is entirely unconventional in the world of diapers, and converts ordinary diaper 12 into the unique combination which has been identified as infant garment 10.

Figure 2:
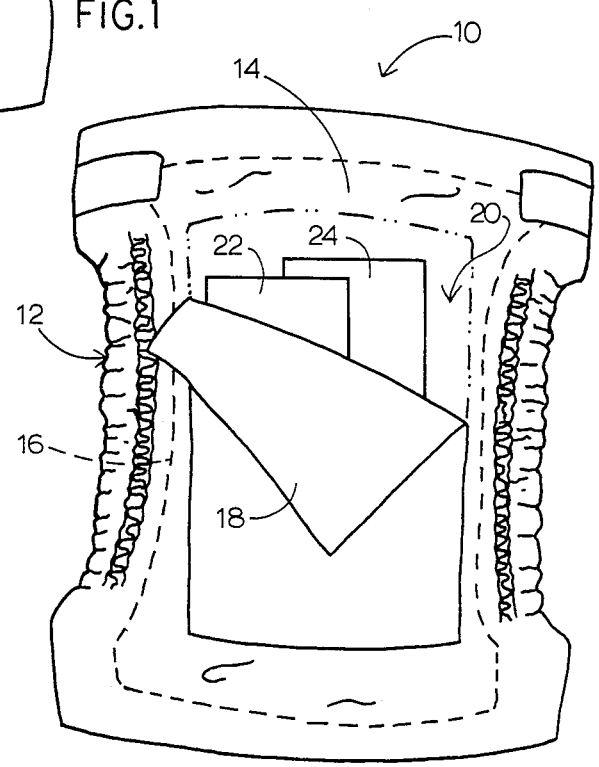
FIG. 2 is like FIG. 1, except that it shows the margin of a piece of material, which partially forms the pocket just mentioned, peeled back, or away, to open that pocket in order to afford access to the stored wipers.

Referring now to FIG. 2 along with FIG. 1, sheet 18 is bonded in such a manner that, at least along a portion of its perimeter, it can easily and quickly be peeled away (See FIG. 2) to open pocket 20, and to expose wipers 22, 24 for immediate removal and use. Such a peel-open capability, vis-a-vis the way in which sheets 14, 18 are joined, can be accomplished, of course, in a variety of well-known ways. The phantom lines in FIG. 2 show where the now peeled-away margins of sheet 18 used to lie.

While, for the purpose of illustration herein, pocket 20 is shown containing two wipers, it should be obvious to those reading this disclosure that different numbers of wipers may be stored in the pocket if so desired.

Further, while, preferably, the product proposed by this invention, as offered to the end user, will arrive with the pocket sealed, and with one or more wipers stored therein, there might be applications where the end user would like to select how many wipers should be so stored. In this kind of a case, the product could be supplied without a wiper initially being tucked in the pocket.

On another matter, while it is preferable to have diaper material 14 form one side of the pocket, this does not necessarily have to be the case. For example, an entire, sealable, but openable, pocket structure, with a peel-away face, could be made independently, and thereafter suitably bonded to the diaper's outer side.

The simplicity and convenience advantages offered by garment 10 should now certainly be apparent. These advantages are the same important ones which were addressed earlier in this disclosure.

Figure 3:
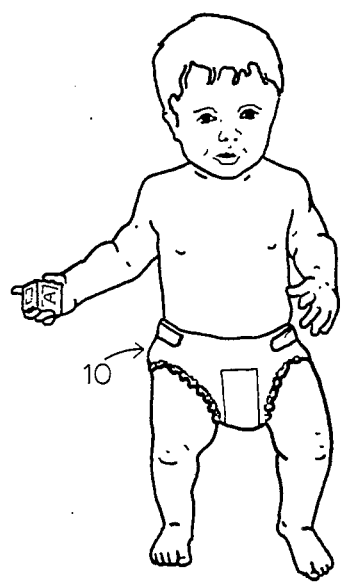
FIG. 3 is a view illustrating the garment of FIGS. 1 and 2 worn on an infant.

An additional advantage, which is made apparent in FIG. 3 where garment 10 is shown worn by an infant, is that the incorporation of the pocket and wipers proposed by the present invention does not add any appreciable bulk to the overall assemblage. Thus, from the point of view of an outside viewer, the garment looks like an otherwise normal, ordinary diaper. From the point of view of an infant wearer, fit and comfort features are substantially the same.

Accordingly, while a preferred embodiment of the invention has been shown and described herein, it is appreciated that variations and modifications may be made without departing from the spirit of the invention.

It is claimed and desired to secure by Letters Patent:

1. A disposable, integrated, multi-piece infant garment comprising
   a diaper including inner and outer sides, with the outer side including an expanse formed of a moisture-impervious material,
   moisture-impervious means joined to and substantially coextensive with said expense and forming therewith a moisture-impervious, sealable but selectively openable pocket, and
   a removable clean-up wiper contained generally coextensively in said pocket.

* * * * *